United States Patent [19]

Grimberg

[11] Patent Number: 5,173,305
[45] Date of Patent: Dec. 22, 1992

[54] COMPOSITION FOR PROTECTION OF OESOGASTRODUODENAL MUCOUS MEMBRANE

[76] Inventor: Georges S. Grimberg, 123 rue de l'Universite, F-75007 Paris, France

[21] Appl. No.: 484,729

[22] Filed: Feb. 22, 1990

Related U.S. Application Data

[60] Continuation-in-part of Ser. No. 178,641, Apr. 7, 1988, abandoned, which is a division of Ser. No. 836,475, Mar. 5, 1986, Pat. No. 4,764,374.

[30] Foreign Application Priority Data

Mar. 6, 1985 [FR] France .................................. 8503306

[51] Int. Cl.$^5$ ...................... A61K 33/06; A61K 33/08; A61K 33/10
[52] U.S. Cl. .................................. 424/682; 424/683; 424/684; 424/686; 424/687; 424/688; 424/689; 424/690; 424/692
[58] Field of Search ................................. 424/682–693

[56] References Cited

U.S. PATENT DOCUMENTS

| | | | |
|---|---|---|---|
| 3,433,643 | 3/1969 | Tatter et al. | 99/59 |
| 3,591,680 | 7/1971 | Greene et al. | 424/601 |
| 3,984,571 | 10/1976 | Chen | 514/781 |
| 4,163,777 | 8/1979 | Mitra | 514/560 |
| 4,468,381 | 8/1984 | Mitra et al. | 424/689 |
| 4,764,374 | 8/1988 | Grimberg, II | 424/687 |

FOREIGN PATENT DOCUMENTS

| | | | |
|---|---|---|---|
| 1254138 | 5/1989 | Canada | 424/687 |
| 112748 | 7/1984 | European Pat. Off. | 424/687 |
| 194202 | 9/1986 | European Pat. Off. | 424/687 |
| 2536994 | 6/1984 | France | 424/687 |
| 2578423 | 9/1986 | France | 424/687 |
| 1097955 | 1/1968 | United Kingdom | 424/687 |
| 1199915 | 7/1970 | United Kingdom | 424/687 |
| 2033915 | 5/1980 | United Kingdom | 424/687 |

*Primary Examiner*—Shep K. Rose
*Attorney, Agent, or Firm*—Browdy and Neimark

[57] ABSTRACT

A pharmaceutical composition is provided for the protection of the oesogastroduodenal mucous membrane, which composition has an active antacid component comprising sufficient guar gum to provide antacid and buffering effect at a pH of from 0.8 to 3.5, and at least one antacid agent other than guar gum in an amount effective as an antacid.

7 Claims, No Drawings

COMPOSITION FOR PROTECTION OF OESOGASTRODUODENAL MUCOUS MEMBRANE

This application is a continuation-in-part of application Ser. No. 07/178,641, filed Apr. 7, 1988, now abandoned which is a divisional of Ser. No. 06/836,475, filed Mar. 5, 1986, now U.S. Pat. No. 4,764,374.

FIELD OF THE INVENTION

The present invention relates to a composition and method for protecting the oesogastroduodenal mucous membrane.

BACKGROUND OF THE INVENTION

Conventional compositions for protecting the oesogastroduodenal mucous membrane are in many different forms. These compositions can, for example, be in the form of suspensions, as granulates, as tablets, or powders. However, despite these various forms, the result sought is not reached, since the purely physical phase is not always obtained and the dispersion of the active ingredient is not good, so that there is not a good lining of the mucous membrane.

Moreover, the various antacids used and the associations therewith do not reasonably cover the various pH ranges which are likely to appear in a patient.

Another disadvantage of conventional antacid compositions is that the pH of the stomach is raised to a level where acid rebound occurs, i.e., the pH of the stomach is raised to a point where the body produces additional acid to lower the pH to a normal level. Prolonged use of such antacids therefore can cause much damage to the oesogastroduodenal mucous membrane because of the additional acid production.

SUMMARY OF THE INVENTION

It is an object of the present invention to overcome the above-noted deficiencies in the prior art.

It is another object of the present invention to provide a pharmaceutical composition for protection of the oesogastroduodenal mucous membrane.

According to the present invention, a pharmaceutical composition is provided which comprises a sufficient amount of guar gum to provide an antacid and buffering effect at a pH ranging from about 0.8 to about 3.5, along with at least one antacid agent in addition to the guar gum in an amount effective as an antacid.

Among the antacids that can be added to the guar gum are aluminum hydroxide, magnesium hydroxide, calcium carbonate, and the corresponding calcium, magnesium, and aluminum oxides, as well as any other salts, oxides, and hydroxides which have been found to be therapeutically useful for protection of the oesogastroduodenal mucous membrane.

Various other features of the invention will become more apparent form the following detailed description. The examples given herein are for purposes of illustration only, and are not limiting of the invention.

The examples given of pharmaceutical compositions according to the present invention can also contain gelling agents, sweeteners, and flavoring agents.

EXAMPLE 1: Ingestible Pharmaceutical Compositions

| | |
|---|---|
| Aluminum hydroxide | 1000 grams |
| Powdered guar gum | 2478 grams |
| Silicone oil | 12.5 grams |
| Sorbitan monooleate | 6.44 grams |
| Polysorbate 80 | 3.22 grams |
| Micronized silica | 50 grams |
| Sugar | 6000 grams |
| Sodium saccharinate | 10 grams |
| Sodium cyclamate | 40 grams |
| Powdered coconut aroma | 200 grams |

The above product is mixed with water water by the patient. The guar gum disperses and then swells, and, at the moment of swelling, captures the aluminum hydroxide. This phenomenon continues in vivo.

The above mixture is readily produced by mixing, and can be packaged into containers or transformed into any convenient galenical form such as tablets, sachets, and the like.

In all cases, if the above composition is dispersed in a liquid medium such as water, whatever the proportions between the product and water, the distribution is rapid even at room temperature or below. The resulting dispersion is homogeneous and need not be subjected to particular stirring apparatus to form a homogeneous dispersion. The consistency of the gel formed will vary only with the amount of water used to form the dispersion and the time the dispersion sits.

For use, it is sufficient to mix the composition with water and to stir with a spoon just until the gel begins to thicken.

EXAMPLE 2

The composition of Example 1 is formed using 500 grams aluminum hydroxide and 500 grams of magnesium hydroxide rather that 1000 grams of aluminum hydroxide.

EXAMPLE 3

The antacid activity of the guar gum in the compositions according to the present invention provides the compositions with a very interesting activity. The compositions are active over a very wide pH range, so that many types of conditions can be treated without causing acid rebound.

The following formula permits one to define four antacid activity zones:

| | |
|---|---|
| a) magnesium hydroxide | 0.5 g |
| b) aluminum hydroxide | 0.5 g |
| c) aluminum phosphate | 0.3 g |
| d) guar gum | 0.3 g | and three buffer power zones:
 a) from pH. 3.5 to pH 3
 b) from pH 2 to pH 1.6
 c) from pH 1 to pH 0.8

The pH measuring technique is that of Vattier.

The compositions of the present invention have additional advantages, including slow activity release kinetics: even thirty minutes after administration, there remains from 36 to 60% of the activity according to the intervention pH.

Simethicone or other substances which reduce gas formation can be included in the formulations according to the present invention.

Test made on animals, including rats and dogs, have yielded excellent results and have shown that, when agents which cause a rapid ulceration of the gastric mucous membrane are administered per se, a treatment of two or three weeks with the composition according to the present invention led to a complete recovery or at least a marked reduction of the ulcerations.

EXAMPLE 4

A pharmaceutical composition is formed from the following ingredients:

| | |
|---|---|
| Aluminum hydroxide | 0.500 g |
| Magnesium hydroxide | 0.500 g |
| Aluminum phosphate | 0.300 g |
| Coated guar gum | 0.200 g |
| Potato starch | 0.300 g |
| Hydroxyethylcellulose | 0.150 g |
| Polyoxyethylene glycol.4000 | 0.250 g |
| Sodium cyclamate | 0.030 g |
| Sodium saccharin | 0.015 g |
| Coconut flavor | 0.050 g |

Tablets were formulated containing 2.295 grams of the above mixture.

A study of the antacid activity of the above tablet and its constituents was carried out using the methods for in vitro evaluation of antacids comprising demonstrating the mechanism of action and determination of the antacid activity at different pH levels approximating those in the human stomach.

EXPERIMENTAL:

The antacid test sample, consisting of one dosage unit, was diluted in 20 ml. of distilled water in placed onto a mechanical stirrer at 37° C.

The pH of the antacid was noted and acid was then added. The volume of acid required to change the pH by one unit or by one tenth unit was noted up to pH 0.5.

Six samples were titrated. The mean quantity of acid required to obtain each pH level was calculated, and the curve of the mean values was then traced.

To determine kinetics of release of antacid activity, acid was added to the dosage unit as prepared above. The acid was added at time zero to adjust the pH to the desired level for at least three seconds. The sample was then stirred at 37° C. and further acid was added at ten, 20, 30, 60, and 120 minutes. The amount of acid added at each time was added together to give the total amount of acid in the titration.

The percentage antacid activity released at the different times was calculated as a fraction of the total alkalinity in order to determine the kinetics of release of the $H^+$—binding sites. The pH levels studies were: pH 3.0, pH 2.0, pH 1.5, and pH 1.0.

It was found that, up to pH 4, the combination of the above tablet in water has a neutralizing effect within the pH range of 1 to 4, representing approximately 2% of the antacid effect.

A powerful buffering effect was found in the pH zone of approximately 3.5. From this pH to pH 0.5, the product both neutralizes and buffers. The neutralizing effect is considerable from pH 3.5 to pH 2.5.

The potency of the buffering effect may be estimated to be 80% of the total antacid effect, and the neutralizing capacity corresponds to approximately 20%.

A study was conducted comparing the pharmacological properties of the tablet as produced above with MAALOX tablets. The MAALOX tablets have the following composition:

| | |
|---|---|
| Aluminum hydroxide | 0.400 g |
| Magnesium hydroxide | 0.400 g |
| Excipient for one tablet | |

Aluminum salts have an antacid activity mainly as a result of their buffering capacity at pH values close to 2.0. Aluminum hydroxide and aluminum phosphate are combined because these two salts have buffering capacities at pH values of about 1.8 and 1.6, respectively, and phosphate ions reduce the risk of phosphorus deficiency that may occur during long term treatment with aluminum hydroxide alone.

Magnesium hydroxide is added to counteract the constipating effect of aluminum, and because of the antacid activity of magnesium. This activity mainly involves a neutralizing effect which may give rise to acid rebound if magnesium hydroxide is used alone.

Guar gum has been shown to be an antacid with a buffering capacity in the pH range close to 1.0. Moreover, the guar gum enables the pharmaceutical tablet to be converted to a gel upon mixing with a liquid such as water.

The conversion of the tablet into a gel considerably reduces the neutralizing effect of the magnesium, and forms an antacid barrier comprising several buffer zones, at pH 3.5 for magnesium, pH 2.0-1.5 for the aluminum salts, and pH 1.0 for guar gum. This activity is slowly released, as demonstrated by the long duration of the antacid effect.

The antacid capacity measured in vitro at pH 3, pH 2, pH 1.5, and pH 1.0 was as follows:

| | |
|---|---|
| pH 3 | 3.22 |
| pH 2 | 7.05 |
| pH 1.5 | 16.61 |
| pH 1.0 | 34.79 | expressed in millimoles of acid bound per gel tablet.

There is no codified method for the in vivo study of antacids. This activity was demonstrated in healthy subjects because of the pharmacological properties observed in vitro.

Since the composition of the present invention has an active buffering capacity at pH values as low as pH 1.0, it was necessary to use a test involving the experimental stimulation of gastric acid secretion.

The stimulation of pepsin and acid secretion by pentagastrin has the advantage of being reproducible. Also, in comparison with the stimulation provided by the ingestion of a meal, this method makes it possible to evaluate both the neutralizing and buffering effects at acid pH values.

The activity of an antacid with a buffering capacity in the pH range of 1-2 may be demonstrated if the antacid is administered 30 minutes after in injection of Pentagastrin. The dose of Pentagastrin used, 6 $\mu$g/kg, gives a nearly maximum response, and the delay of 30 minutes corresponds to the time taken for secretion to reach a plateau.

As the tablet forms a gel in the presence of water, the controlled trial included the intragastric administration of an identical amount of this solvent in order to evaluate the antacid effect of the water itself when used as a vehicle.

The study of the antacid activity was continued for one hour after the intragastric administration of the drug. After this time interval, part of the antacid had left the stomach.

The study of the composition of the present invention, designated herein as SERO12, was carried out in a randomized manner with the control being one MAALOX tablet. The tablets were administered mixed with 60 ml water.

The controlled test also included, thirty minutes after the injection of pentagastrin, the administration of 60 ml of water by gastric intubation.

Sequence C

—$T_0$: injection of 6 µg/kg pentagastrin
—$T_{+30}$ minutes: L administration of 60 ml of water by gastric intubation This sequence was carried out in all subjects in order to analyze the response of the subjects to pentagastrin injection for 60 minutes.

Sequence A

—$T_0$: injection of 6 µg/kg pentagastrin
$T_{30}$ minutes: administration of one SERO12 tablet dissolved in 60 ml of water by gastric intubation Sequence B $T_0$: injection of 6 µg/kg pentagastrin
$T_{30}$ minutes: administration of one MAALOX tablet dissolved in 60 l of water by gastric intubation Sequences A and B were randomized to counteract any effect of the order of administration.

As far as possible, the three sequences took place at a fixed time on a fixed date with a time interval of one week between each test.

The subjects fasted overnight and refrained from smoking for 12 hours.

At 8 AM, a nasogastric tube was inserted into the stomach. The subject then was placed in the left lateral decubitus position, and remained in his position throughout the experiment to prevent the gastric contents from escaping through the pylorus, taking care not to swallow the saliva.

The water tests was performed, and all the basal secretions were collected for 15 minutes. Pentagastrin was injected at time T0 and aliquots of the secretions were collected every ten minutes.

At $T_{+30}$ minutes, a larger aliquot was taken, and the 60-ml of water alone or carrying the test products was administered with the tube. The acid concentration of a fraction of this aliquot was immediately assayed, and the test was only continued if this were greater than 45 mmol/l.

Aliquots of the secretions were then taken every five minutes up to $T_{+90}$ minutes. Each aliquot contained approximately 5 ml of the gastric juices.

The acidity was measured using three methods:

1) titration with sodium hydroxide at pH 7.0 to measure the titratable acidity of the sample. This value can be used to theoretically evaluate the effect of pentagastrin stimulation and the reduction in the acidity as a result of drug action.

2) titration with sodium bicarbonate at pH 6.4. This titration investigates physiological phenomena as it gives the concentration of pancreatic bicarbonate required for the intraduodenal neutralization of the acid chymus produced by the stomach.

The results of both of the above titrations were expressed in millimoles of acid per liter, and can be statistically analyzed with the usual tests.

c) measurement of the pH with a combined glass-/calomel electrode to record the electromotive force created by the hydrogen ions in the complex solution provided by the gastric fluids. Because of the logarithmic expression of the pH, the results could not be compared using conventional statistical methods. Therefore, nonparametric tests were used.

The proteolytic activity of the gastric juice is stimulated by pentagastrin. This may be reduced by antacids when the pH reaches a level at which the pepsins are inactivated, or by a direct effect of the antacids.

The method used was based on the determination of the total proteolytic activity from the initial reaction rate using human hemoglobin as a substrate.

In order to study of the activity of each product, the following were analyzed on each aliquot:

1) acid concentration (mmol/l) by titration with sodium hydroxide at pH 7 and titration with sodium bicarbonate at pH 6.4.
2) measurement of the pH
3) pepsin concentration.

The gastric juices collected were stored at +4° C. in each of the centers, and were then sent to a laboratory where all of the assays were performed in order to eliminate any errors due to the analytical methods.

Both male and female subjects, less than 40 years old, participated in the study. All of the subjects were in good health, and gave their informed consent. None of the subjects had received medication during the week prior to the study. None of the subjects consumed excessive amounts of alcohol.

The order of administration of the products was as follows:

| Dr. Boisson (Notre Dame du Bon Secours Hospital) | | | |
|---|---|---|---|
| Subject No. 1 | C | A | B |
| Subject No. 2 | C | B | A |
| Subject No. 3 | C | A | B |
| Dr. Vallot (Bichat Hospital) | | | |
| Subject No. 4 | C | B | A |
| Subject No. 5 | C | A | B |
| Subject No. 6 | C | B | A |

The mean results (titration with NaOH, titration with sodium bicarbonate, pepsin concentration) are given in Tables 1–3.

The "mean" pH values are given in Table 4.

Table 5 summarizes the results of the comparisons of the pH by non-parametric statistical methods.

Table 6 gives for each subject the time (in minutes) during which the pH was maintained above the control values (water).

TABLE 1

TITRATION WITH SODIUM HYDROXIDE
(in mmol H+)
Mean and estimated standard deviation

| Time minutes | Product | C (WATER) m | SD | A (SERO 12) m | SD | B (MAALOX) m | SD | STATISTICAL COMPARISON |
|---|---|---|---|---|---|---|---|---|
| 0  | 0  | 16.0 | (14.9) | 20.0 | (16.7) | 20.7 | (17.1) | |
| 10 | 1  | 53.3 | (32.5) | 56.7 | (19.4) | 52.0 | (39.5) | |
| 20 | 2  | 79.3 | (21.0) | 71.3 | (15.5) | 74.3 | (34.9) | |
| 30 | 3  | 96.8 | (18.5) | 90.4 | (11.9) | 89.6 | (36.8) | |
| 35 | 4  | 42.3 | (31.9) | 16.7 | (12.6) | 38.8 | (40.9) | |
| 40 | 5  | 58.0 | (25.0) | 31.0 | (25.2) | 31.0 | (23.9) | A and B < C |
| 45 | 6  | 63.3 | (27.9) | 25.7 | (23.8) | 41.3 | (27.4) | A < B < C |
| 50 | 7  | 67.7 | (26.6) | 27.3 | (24.5) | 46.0 | (29.5) | A < B < C |
| 55 | 8  | 67.3 | (33.2) | 29.3 | (24.2) | 50.0 | (33.1) | A < B < C |
| 60 | 9  | 67.0 | (34.2) | 40.7 | (20.1) | 53.0 | (29.4) | A < C |
| 65 | 10 | 68.0 | (30.7) | 40.7 | (22.6) | 48.7 | (32.8) | A < C |
| 70 | 11 | 68.3 | (30.1) | 45.3 | (24.8) | 51.3 | (31.3) | |
| 75 | 12 | 68.0 | (30.9) | 48.0 | (26.6) | 54.3 | (32.0) | |
| 80 | 13 | 71.7 | (32.4) | 50.3 | (30.3) | 51.7 | (34.9) | |
| 85 | 14 | 71.3 | (33.2) | 50.7 | (27.5) | 50.7 | (34.0) | |
| 90 | 15 | 65.7 | (32.4) | 48.3 | (29.8) | 41.3 | (22.9) | |

TABLE 2

TITRATION WITH BICARBONATE
(in mmol H+)
Mean and estimated standard deviation

| Time minutes | Product | C (WATER) m | SD | A (SERO 12) m | SD | B (MAALOX) m | SD | STATISTICAL COMPARISON |
|---|---|---|---|---|---|---|---|---|
| 0  | 0  | 21.3  | (20.5) | 27.0  | (21.5) | 27.3  | (24.1) | |
| 10 | 1  | 65.3  | (35.6) | 73.0  | (26.6) | 67.3  | (42.7) | |
| 20 | 2  | 97.0  | (27.0) | 89.7  | (19.5) | 90.7  | (39.1) | |
| 30 | 3  | 116.8 | (16.2) | 106.8 | (13.5) | 110.0 | (29.0) | |
| 35 | 4  | 50.0  | (36.9) | 18.0  | (17.6) | 26.7  | (24.9) | A and B < C |
| 40 | 5  | 69.0  | (28.7) | 37.3  | (34.3) | 41.3  | (27.8) | A and B < C |
| 45 | 6  | 79.3  | (25.5) | 30.0  | (27.2) | 52.7  | (31.7) | A < B < C |
| 50 | 7  | 82.7  | (28.6) | 31.7  | (28.0) | 56.7  | (31.8) | A < B < C |
| 55 | 8  | 79.0  | (32.9) | 37.3  | (29.5) | 61.0  | (33.6) | A < B < C |
| 60 | 9  | 82.7  | (37.0) | 50.3  | (26.9) | 64.0  | (31.5) | A < C |
| 65 | 10 | 81.0  | (33.6) | 48.37 | (25.5) | 57.3  | (24.7) | A < C |
| 70 | 11 | 81.0  | (33.4) | 54.3  | (28.0) | 63.0  | (33.0) | |
| 75 | 12 | 82.7  | (34.2) | 56.2  | (29.3) | 67.3  | (33.9) | |
| 80 | 13 | 86.7  | (35.6) | 65.3  | (37.0) | 65.3  | (39.0) | |
| 85 | 14 | 89.0  | (37.4) | 66.3  | (39.5) | 61.7  | (39.9) | |
| 90 | 15 | 81.3  | (37.1) | 65.0  | (38.8) | 57.7  | (28.8) | |

TABLE 3

PEPSIN
(pepsin units/ml)
Mean and estimated standard deviation

| Time minutes | Product | C (WATER) m | SD | A (SERO 12) m | SD | B (MAALOX) m | SD | STATISTICAL COMPARISON |
|---|---|---|---|---|---|---|---|---|
| 0  | 0  | 1.08 | (1.31) | 3.60 | (2.66) | 3.40 | (2.05) | |
| 10 | 1  | 6.28 | (3.19) | 6.08 | (0.98) | 6.18 | (2.35) | |
| 20 | 2  | 8.04 | (2.35) | 6.50 | (0.55) | 6.92 | (1.55) | |
| 30 | 3  | 7.89 | (2.12) | 6.00 | (0.90) | 5.91 | (2.39) | |
| 35 | 4  | 4.42 | (0.84) | 3.55 | (1.55) | 3.13 | (0.81) | |
| 40 | 5  | 4.27 | (1.32) | 4.06 | (1.48) | 4.07 | (1.85) | |
| 45 | 6  | 4.83 | (1.42) | 3.31 | (1.05) | 4.22 | (1.85) | |
| 50 | 7  | 4.86 | (1.79) | 3.31 | (1.20) | 4.65 | (1.49) | |
| 55 | 8  | 4.95 | (1.87) | 3.64 | (0.93) | 5.32 | (1.74) | |
| 60 | 9  | 4.92 | (1.15) | 4.47 | (1.39) | 5.07 | (1.52) | |
| 65 | 10 | 5.13 | (1.49) | 4.67 | (1.59) | 4.94 | (1.43) | |
| 70 | 11 | 5.67 | (1.72) | 5.37 | (1.68) | 5.17 | (1.30) | |
| 75 | 12 | 5.46 | (1.51) | 5.57 | (1.92) | 5.09 | (1.10) | |
| 80 | 13 | 5.60 | (1.99) | 5.72 | (1.83) | 5.00 | (1.10) | |
| 85 | 14 | 5.41 | (2.22) | 5.87 | (1.90) | 5.29 | (2.19) | |
| 90 | 15 | 5.41 | (2.50) | 6.25 | (2.36) | 5.14 | (1.53) | |

TABLE 4

| | | "MEAN" pH | | |
|---|---|---|---|---|
| Time minutes | C Product | A (CONTROL) | A (SERO 12) | B (MAALOX) |
| 0 | 0 | 4.49 | 3.83 | 3.34 |
| 10 | 1 | 1.85 | 1.53 | 2.12 |
| 20 | 2 | 1.54 | 1.32 | 1.43 |
| 30 | 3 | 1.30 | 1.26 | 1.66 |
| 35 | 4 | 2.31 | 3.34 | 3.24 |
| 40 | 5 | 1.53 | 3.31 | 2.58 |
| 45 | 6 | 1.47 | 3.55 | 2.36 |
| 50 | 7 | 1.45 | 3.49 | 2.16 |
| 55 | 8 | 1.50 | 3.06 | 2.27 |
| 60 | 9 | 1.52 | 2.50 | 2.10 |
| 65 | 10 | 1.48 | 2.41 | 2.20 |
| 70 | 11 | 1.47 | 2.22 | 2.05 |
| 75 | 12 | 1.46 | 2.11 | 2.15 |
| 80 | 13 | 1.45 | 2.09 | 2.26 |
| 85 | 14 | 1.46 | 2.09 | 2.37 |
| 90 | 15 | 1.45 | 2.18 | 2.45 |

TABLE 5

| | | pH | |
|---|---|---|---|
| Time minutes | Sample no | FRIEDMAN'S CHI 2 (overall comparison) | WILCOXON'S T-TEST (2 × 2 comparison) |
| 0 | 0 | | |
| 10 | 1 | | |
| 20 | 2 | | |
| 30 | 3 | | |
| 35 | 4 | | |
| 40 | 5 | DS | A > C |
| 45 | 6 | DS | A > C and B |
| 50 | 7 | DS | A > C and B |
| 55 | 8 | | |
| 60 | 9 | | |
| 65 | 10 | | |
| 70 | 11 | | |
| 75 | 12 | | |
| 80 | 13 | | |
| 85 | 14 | | |
| 90 | 15 | | |

TABLE 6

DURATION OF THE MAINTENANCE OF THE pH ABOVE THE CONTROL VALUE (WATER) (EXPRESSED IN MINUTES)

| | product | |
|---|---|---|
| Subject | A | B |
| SUBJECT 1 | 60 | 25 |
| SUBJECT 2 | 60 | 50 |
| SUBJECT 3 | 20 | 5 |
| SUBJECT 4 | 60 | 60 |
| SUBJECT 5 | 60 | 60 |
| SUBJECT 6 | 60 | 0 |
| Mean (minutes) | 53.3 | 33.3 |
| SD | 16.3 | 27.1 |

The results show that the subjects were perfectly matched before each test both for basal gastric secretion and for the secretory response to pentagastrin, as there were no significant differences in the mean acid and pepsin concentrations at time 0 before each of the tests, and there were no significant differences in the mean acid and pepsin concentrations in the gastric juices collected 10, 20, and 30 minutes after pentagastrin injection, before each of the tests.

The composition of the present invention, SERO12, had an effective antacid action. When the acid concentrations measured in mmol/l were compared every five minutes after the administration of each of the products, there was a significant difference between SERO12 and the control (water) from 5 minutes by titration at pH 6.4 with sodium bicarbonate, and from ten minutes by titration at pH 7 with sodium hydroxide.

This significant difference disappeared 40 minutes after product administration.

The antacid activity of SERO12 was more potent and had a longer duration of action than MAALOX. A significant difference between MAALOX and water was observed at the same time as with SERO12, but it disappeared earlier, about 30 minutes after product administration. There was a significant difference between SERO12 and MAALOX at 15, 20, 25, and 30 minutes after product administration.

With regard to the pH data, there was a significant difference between SERO12 and the control at 10, 15, and 20 minutes after administration, and a significant difference between SERO12 and MAALOX 15 and 20 minutes after administration, confirming the efficacy of SERO12 relative not only to the control, but also to the reference product, MAALOX. The lack of any significant change between 20 and 40 minutes after product administration when the acid concentrations as measured by titration were still significantly reduced is probably explained by the fact that the product mainly has a buffering effect during this period.

With regard to the pepsin concentrations, although the values recorded with SERO12 were slightly lower, there was no significant difference between the results for SERO12 and the control.

Another study was conducted to evaluate the antacid effect and the reaction kinetics of guar gum in vivo at a dose of one gram of guar gum.

Six healthy male and female volunteers, between 20 and 50 years of age, were selected for the study. Each subject received, under the same experimental conditions as in the study described above, one gram of coated guar gum having the following composition:

| Guar gum | 100 grams |
|---|---|
| Simethicone | 0.5 gram |
| Excipient | q.s. |

The test was conducted as described above, with the following sequences:

$T_0$: injection of pentagastrin (6 μg/kg)

$T_{30}$ minutes: Administration by gastric intubation of one gram of guar gum suspended in 60 ml water.

Aliquots of the gastric juices were recovered every 15 minutes from T30 minutes to T90 minutes.

As in the study described above, three methods were used to measure the acidity:

1) titration with sodium hydroxide at pH 7.0
2) titration with sodium bicarbonate at pH 6.4
3) measurement of the pH To determine the proteolytic activity, the pepsin concentration was measured in U/ml.

The mean and the SEM of the titrations with sodium hydroxide and sodium bicarbonate, and the proteolytic activity and the residual values expressed as a percentage of the response are shown in Table 7. The "mean" pH values are shown in Table 8.

TABLE 7

1 GRAM GUAR GUM (ALL SIX SUBJECTS)

| | Concentration | | |
|---|---|---|---|
| Time minutes | mmol H+ (NaOH) | mmol H+ (CO$_3$HNa) | PEPSIN PU/ml |

TABLE 7-continued

| 1 GRAM GUAR GUM (ALL SIX SUBJECTS) | | | |
|---|---|---|---|
| 30 | 94.3 ± 15.0 | 112.6 ± 13.4 | 6.63 ± 1.08 |
| 45 | 64.3 ± 18.2 | 77.3 ± 18.4 | 3.58 ± .074 |
| 60 | 72.6 ± 15.9 | 83.3 ± 17.0 | 4.45 ± 0.77 |
| 75 | 68.6 ± 15.3 | 80.6 ± 16.1 | 5.21 ± 1.08 |

RESIDUAL CONCENTRATION EXPRESSED AS A PERCENTAGE OF THE RESPONSE TO PENTAGASTRIN

| Time minutes | Concentration | | |
|---|---|---|---|
| | (NA OH) | ($CO_3$ HNA) | (Pepsin) |
| 45 | 68% | 68% | 53% |
| 60 | 76% | 74% | 67% |
| 75 | 72% | 71% | 78% |
| 90 | 48% | 46% | 63% |

TABLE 8

| "mean pH" | |
|---|---|
| Time minutes | pH |
| 30 | 1.09 |
| 45 | 1.27 |
| 60 | 1.28 |
| 75 | 1.28 |
| 90 | 2.81 |

As can readily be seen from the above, guar gum caused a reduction in the acidity stimulated by pentagastrin of approximately 30 percent at each time (45 minutes, 60 minutes, 75 minutes) and approximately 50% at 90 minutes. A parallel reduction in the proteolytic activity was also observed. There was a slight increase in the "mean" pH at the first three times, and a large increase at 90 minutes.

The results of this study show that, at a dose of one gram, guar gum exhibits a delayed antacid effect in vivo. The reaction kinetics therefore differ form those of other antacids, and this might partly explain the longer duration of action of SERO12 as compared to MAALOX.

A comparison was conducted to compare the pharmacologic effect in vitro of the formulation according to the present invention.

Two preparations contained in common the following mineral antacid salts: aluminum phosphate, aluminum hydroxide, and magnesium hydroxide, but they differed by the presence of 1 gram of guar gum in the sachet, and 0.2 gram of guar gum in the tablet.

The study was conducted to compare the two forms using an artificial stomach in different milieus, including an aqueous solution of hydrochloric acid, 1N, and a 0.1N solution of hydrochloric acid enriched in proteins with a final concentration of from 1 to 5% of meat extract.

The model of the artificial stomach has already been described in an article published in *Digestive Disease and Science*. It was used here to simulate a gastric hypersecretion in a medium both poor in and enriched in proteins. This model includes a gastric reservoir, which is under a part of a flux of secretion, flux S2, constant at 3 ml/min of 0.1N hydrochloric acid or of gastric juice according to the experiments and equally below a flux S3 of variable emptying, the emptying being slow, rapid, or equal to the rate of filling.

The gastric content comprises at time 0 a volume of 100 ml of hydrochloric acid or gastric juices, the secretion represented by the same liquid, hydrochloric acid or gastric juices, the complete system remaining at a constant pH which is 1.0 until the introduction of the 0.1N hydrochloric acid.

The introduction of an antacid in the gastric contents modified the pH of the contents which evolved as a function of the secretion and the simulated draining. This system made it possible to calculate the number of mmol consumed by the antacid to return to the initial pH, i.e., to measure the resistance induced by the antacid in the raising of the pH.

A combined electrode placed in the gastric contents permitted registration of the variations of the pH in the stomach contents, this electrode being connected to a pH-meter itself in relation to a recorder.

The experiment was conducted with pH measurements until the pH of the gastric contents returned to the initial pH.

The analysis of the graph of the pH-meter included the following:

1) measure of the maximum pH;
2) measure of the time expressed in minutes over and above the level of the reference pH;
3) calculation of the antacid capacity expressed in mmol of acid consumed to reach the level of the reference pH, counting form the quantity of acid at time 0 in the stomach and the quantity of acid which has been added.
4) determination of the neutralization activities and the buffer capacity and the influence of the dilution as a consequence of the mechanisms implicated in the previous examples.

The comparison of the activity of the compressed Moxydar form and of the Moxydar sachet was obtained by using a second system of the "stomach" in which the evolution of the pH was registered by a second series of pH-meters. This permits a comparison of the variations of pH obtained by using the sachet or the compressed tablet.

The experiments were conducted in a milieu of 0.1N hydrochloric acid with three emptying cycles indicated at 1.5, 3, and 4.5 minutes. They were also conducted using a pool of human gastric juices at pH 1.0 and a concentration of acid of 90 mmol/l in using the same cycle of emptying. Finally the system used an addition of meat extracts to the 0.1N solution of hydrochloric acid such that the final concentration was from about 1 to 5%. The experiments were repeated and were concerned with the emptying time of 3 and 4.5 minutes.

In a milieu of 0.1N hydrochloric acid, the results are shown in Table 9. The addition of the two forms of the composition of the present invention resulted in an elevation of the pH of the gastric contents from 1.0 to 5.4 with the sachet, and from 1.0 to 4.5 with the tablet.

TABLE 9

MOXYDAR Tablet or Sachet Added to 100 ml 0.1NHcl
pH Maximum and time (min.) to reach the considered pH level

| Emptying flux (ml/min) | 1.5 | | 3.0 | | 4.5 | |
|---|---|---|---|---|---|---|
| Form | Tablet | Sachet | Tablet | Sachet | Tablet | Sachet |
| pH maximum | 4.5 | 5.4 | 4.7 | 5.7 | 5.7 | 6.5 |
| Time to reach | | | | | | |
| pH 4.0 | 0.5 | 2 | 0.5 | 7 | 1 | 10 |
| pH 3.0 | 23 | 35 | 15 | 29 | 19 | 24 |
| pH 2.0 | 53 | 110 | 37 | 40 | 28 | 31 |
| pH 1.5 | 145 | 196 | 57 | 52 | 34 | 35 |
| pH 1.2 | 210 | 206 | 89 | 89 | 48 | 50 |
| pH .0 | 300 | 360 | 130 | 135 | 74 | 74 |
| mmol H+ | 100 | 118 | 49 | 50.5 | 32.2 | 32.2 |

TABLE 9-continued

Consumed
to reach

Under the effect of the stimulated secretion, one could observe a diminution of the pH, rapid at first, and then stabilized with a small decrease towards pH 3.5, then towards pH 2.0, a and then towards pH 1.5-1.2, these zones corresponding to the establishment of the buffer capacities due respectively to the association of the aluminum-magnesium, to the aluminum phosphate, and to the aluminum hydroxide. In the function of the emptying flux, the delays to return to the initial pH were variable, either for the tablet, from 300 min in response to the slow emptying, of 130 min for the equal emptying, and 74 min in response to the rapid emptying. These delays corresponded to the consumption respectively, of 100, 49, and 32.2 mmol of acid. Using the sachet form, the delays were 360 min in response to the slow emptying, 135 min in response to the equal rate of emptying, and 74 minutes in response to the rapid emptying, corresponding to the consumption of 118, 50.5, and 32.2 mmol of acid.

The rules of correlation can be established between the agreement of the secretion and of emptying and the consumption of hydrogen ions, the equations of the regressions, being, respectively,:

for the tablet: $Y = 50.68X - 1.44$ $(r=1000)$
for the sachet: $Y = 64.81X - 12.17$ $(r=0.999)$ The slope of these equations represents the intensity of the antacid activity as a function of the intraluminar gastric flux and this result emphasizes that the sachet form has an antacid intensity slightly more important than that developed by the tablet.

The mechanisms of the antacid action are based upon a weak neutralization activity and on three buffering zones, one zone between pH 3.5 and pH 3.8, a second zone around pH 2.0, and a third zone around pH 1.5-1.2, at which the additive effect of the dilution induced by the antacid mechanisms develops as above.

In the environment of human gastric juices at pH 1.0 and 90 mmol/l, the results are shown in Table 10.

TABLE 10

MOXYDAR Tablet or Sachet Added to 100 ml Human Gastric Juice (pH 1.0-90 mmol/l)
Maximum pH and time (min.) to reach the considered pH level

| Emptying time (ml/min) | 1.5 | | 3.0 | | 4.5 | |
|---|---|---|---|---|---|---|
| Forme | Tablet | Sachet | Tablet | Sachet | Tablet | Sachet |
| pH maximum | 2.45 | 5.6 | 4.1 | 5.75 | 3.05 | 4.8 |
| Time to reach | | | | | | |
| pH 4.0 | — | 3 | 1 | 5 | — | 2 |
| pH 3.0 | — | 25 | 14 | 23 | 1 | 17 |
| pH 2.0 | 19 | 48 | 33 | 34 | 24 | 27 |
| pH 1.5 | 76 | 40 | 45 | 47 | 34 | 38 |
| pH 1.2 | 160 | 180 | 90 | 93 | 51 | 48 |
| pH 1.0 | 320 | 370 | 120 | 120 | 62 | 62 |
| mmol H+ Consumed to reach | 95.4 | 108 | 41.4 | 41.4 | 25.7 | 25.7 |

The phenomena observed are comparable to those which were observed in the aqueous hydrochloric acid environment with, always in response to the slow emptying, a lesser elevation of the pH with the tablet than with the sachet. The delays in returning to the pH of the gastric juices were a function of the emptying time, respectively for the tablet, of 320, 120, and 62 in and of 370, 120, and 62 for the sachet form. The consumption of hydrogen ions to return to a pH 1.0 were respectively, of the tablet form, 95.4, 41.4, and 25.7 mmol for the emptying considered, and for the sachet form, 108, 41.4, and 25.7 mmol. It is equally possible to establish a correlation between the agreement of the secretion and emptying and the consumption of hydrogen ions. These equations are:

for the tablet: $Y = 52.4X - 9.19$ $(r=1000)$
for the sachet: $Y = 62.57X - 17.95$ $(r=0.998)$ It appears also in the case of gastric juices that the intensity of the antacid activity of the sachet form is slightly superior to that of the tablet. It should be noted that the slope of the equations for the gastric juices are similar to those for the aqueous hydrochloric acid environment.

In the case where the final concentration of proteins is approximately 1%, the antacid effect observed is shown in Table 11. This is essentially represented by a neutralization activity in which there is a buffering capacity around pH 1.2, which is based upon the liberated aluminum ions.

The delay in returning to the initial pH vary with the emptying time used. These are 1623 min for the two forms, sachet and tablet, in response to 3 ml/min of emptying and between 67 and 63 minutes in response to rapid emptying.

The resistance to the lowering of the pH is, for the tablet form, 58.6 mmol and 30.1 mmol respectively for the emptying flux of 3 and of 4.5 ml/min, respectively, and for the sachet form, it is on the same order, from 58.6 mmol in response to 3 ml/min and of 28.9 mmol in response to the rapid emptying.

With a final protein concentration of about 5%, the antacid effect is essentially supported by the development of the neutralization activity, and there is no more buffering activity. The results are shown in Table 12. The delays in returning to the initial pH are 140 and 53 min for the tablet in response to an emptying flux of 3, and 4.5 ml.min, and for the sachet form, 182 to 67 min, which corresponds to a consumption of acid to return to the base of pH required between 52 and 25.9 mmol of acid for the tablet and 64.6 and 30.1 mmol for the sachet form.

The two forms studied contained identical amounts of antacid mineral salts represented by aluminum hydroxide, aluminum phosphate, and magnesium hydroxide. The essential difference between the two preparations is in the amount of the guar gum in the sachet form of 1.0 gram, as opposed to an amount of 0.2 g in the tablet form.

The results obtained give the appearance that the delay to return to the initial pH after introduction of the two forms into the artificial stomach system are longer when it is a question of the sachet form or when it is a question of the tablet form, which can be interpreted as a consumption of hydrogen ions more important for this form. The slopes of the correlation between the agreement of the emptying and secretion and the consumption of acid ions show also that the sachet form has a tendency to develop an superior antacid activity to the tablet form. The antacid mechanisms are rather close for the two forms: weak neutralization capacity by the augmentation of the pH of the gastric contents, then reduction of the pH under the effect of the simulated secretion with the appearance of the successive buffer capacities between pH 3.5-3.8, corresponding to the association of the aluminum and magnesium ions, toward about pH 2.0 corresponding to the buffer effect of the aluminum phosphate, and toward about pH 1.5-1.2 corresponding to the buffer effect of the aluminum hydroxide.

The guar gum appears to slow down the distribution of the antacid effect in the sachet form in a manner somewhat more distinct that in the tablet form. When these preparations are put into an environment enriched in proteins, the phenomena observed are identical for the two preparations, the neutralization effect and then the buffer capacity while the protein concentration is about 1%, and total disappearance of the buffering capacity when the concentration of proteins is more elevated or only neutralization activity is with the proteins.

The consumption of hydrogen ions is also slightly superior to that observed in the aqueous hydrochloric acid environment, but there does not appear to be a benefit in the addition of these forms to an environment rich in proteins.

From the above, it can be seen that the sachet form has an antacid activity slightly superior to that of the tablet form. The enrichment of the guar gum in this preparation has a tendency to liberate the antacid activity more slowly and also to retard the time required to return to the initial pH into which the antacid has been introduced.

The foregoing description of the specific embodiments will so fully reveal the general nature of the invention that others can, by applying current knowledge, readily modify and/or adapt for various applications such specific embodiments without departing from the generic concept, and therefore such adaptations and modifications are intended to be comprehended within the meaning and range of equivalents of the disclosed embodiments. It is to be understood that the phraseology or terminology herein is for the purpose of description and not of limitation.

What is claimed is:

1. A pharmaceutical composition in powder form for the protection of the oesogastroduodenal mucous membrane having active antacid components, wherein said active antacid components consist essentially of sufficient guar gum to provide antacid and buffering effect at a pH of from 0.8 to 3.5, and at least one antacid agent other than guar gum in an amount effective as an antacid, said guar gum and at least one antacid agent other than guar gum being in a ratio of about 2.5:1 to about 2:13.

2. The composition according to claim 1 wherein said antacid agent other than guar gum is selected from the group consisting of aluminum hydroxide, magnesium hydroxide, calcium carbonate, aluminum oxide, magnesium oxide, calcium oxide, and mixtures thereof.

3. The composition according to claim 1 further including an amount of simethicone effective to relieve meteorism.

4. The composition according to claim 1 further including pharmaceutically acceptable excipients in effective amounts.

5. The pharmaceutical composition according to claim 2 having the following formulation:

| | | |
|---|---|---|
| a) guar gum | 0.2 g |
| b) magnesium hydroxide | 0.5 g |
| c) aluminum hydroxide | 0.5 g |
| d) aluminum phosphate | 0.3 g |

6. The pharmaceutical composition according to claim 4 in the form of a tablet.

7. The composition according to claim 2 wherein the at least one antacid other than guar gum is aluminum hydroxide.

* * * * *